Figure 1:
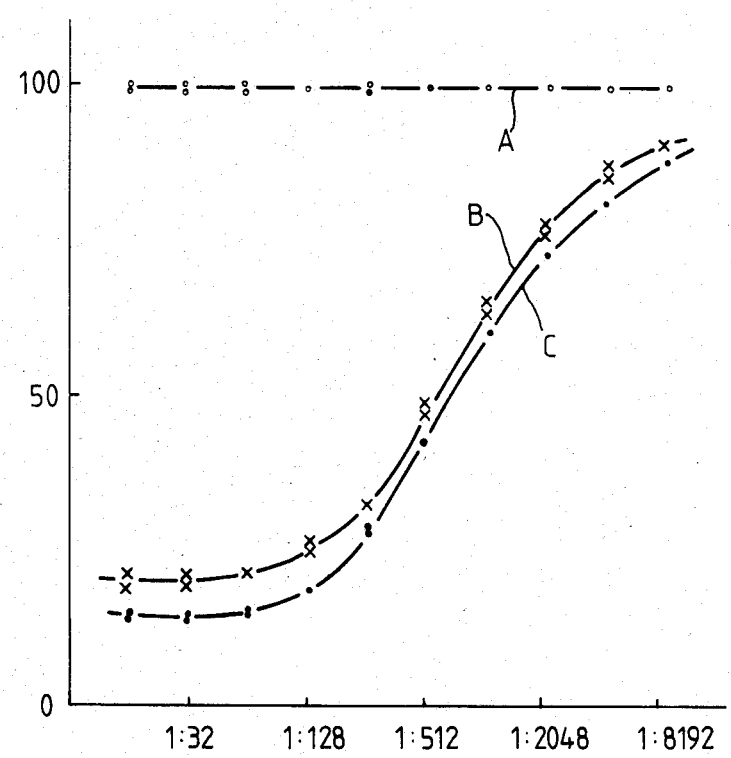

United States Patent [19]

Sidki et al.

[11] Patent Number: 4,637,985

[45] Date of Patent: Jan. 20, 1987

[54] ASSAY PROCESSES AND MATERIALS THEREFOR

[75] Inventors: Ahmad M. Sidki; David S. Smith, both of London, England

[73] Assignee: Internationale Octrooi Maatschappij "Octropa" B.V., Rotterdam, Netherlands

[21] Appl. No.: 536,238

[22] Filed: Sep. 27, 1983

[30] Foreign Application Priority Data

Sep. 27, 1982 [GB] United Kingdom ............... 8227536

[51] Int. Cl.$^4$ ............... G01N 33/542; G01N 33/544; G01N 33/553
[52] U.S. Cl. .................................... 436/518; 436/526; 436/530; 436/536; 436/537; 436/800; 436/808; 436/815; 436/817; 436/825; 436/826; 436/546; 422/61
[58] Field of Search ............... 436/536, 537, 546, 800, 436/825, 518, 526, 530; 422/61

[56] References Cited

U.S. PATENT DOCUMENTS

| | | | |
|---|---|---|---|
| 4,160,818 | 7/1979 | Smith et al. | 436/536 |
| 4,252,783 | 2/1981 | Kam et al. | 436/825 |
| 4,492,762 | 1/1985 | Wang et al. | 436/536 |

FOREIGN PATENT DOCUMENTS 104926 4/1984 European Pat. Off. ............ 436/536

OTHER PUBLICATIONS

*Immuno Assays for the 80s*, Voller et al, Eds., University Park Press, Baltimore, 1981, p. 96.

Primary Examiner—Christine M. Nucker
Attorney, Agent, or Firm—Cushman, Darby, & Cushman

[57] ABSTRACT

A process of carrying out a specific binding assay, for the qualitative detection or quantitative or semi-quantitative determination of an analyte which forms a component of a specific binding reaction, using a labelled conjugate form of a derivative or analogue of one of the relevant specific binding partners, said labelled form being capable of emitting delayed luminescence upon photo-excitation, characterized in that the labelled conjugate form of one of the relevant specific binding partners comprises a derivative or analogue of the specific binding partner with a derivative of a luminescent substance which shows a delayed light emission upon photoexcitation, the delayed light emission of which is subject to quenching by molecular oxygen, and characterized further in that the assay is carried out by the use of a time-resolved photometric method in the presence of an effective amount of a quench-inhibiting substance able to prevent quenching by molecular oxygen.

6 Claims, 5 Drawing Figures

ASSAY PROCESSES AND MATERIALS THEREFOR

This invention concerns improvements in immunoassays and other specific binding assays, and also materials suitable for carrying out the improved assays.

In this specification, 'assay' means a process for the qualitative detection or for the quantitative or semi-quantitative determination of a material ('analyte') to be tested for. The invention particularly concerns specific binding assays. Of these the most common are the immunoassays, involving binding interactions of antigens or haptens (such as hormone or drug molecules) with their corresponding antibodies. (However, among specific binding assays there are also those based on analogous specific binding interactions of substances other than antibodies, e.g. avidin and biotin, thyroid substances and TBG, etc. It is understood that these other interactions can equally form part of the basis for assays of the type with which this specification is concerned.)

Such assays are based on the use of a labelled form of one of the specific binding partners. They are arranged so that a specific binding reaction takes place in which the proportions of the labelled form in the complexed state and the uncomplexed state at the end of the assay reaction depend on the quantity of analyte present in the system. Then the distribution of labelled material is determined by some appropriate method, involving the measurement of activity of the label in the reaction mixture or in some relevant portion thereof, e.g. the liquid or solid phase in the case of a heterogeneous reaction. In the prior art, labels which have been used include radiolabels, enzyme labels, fluorescent labels and electron spin-resonant labels. Appropriate detectors of corresponding kinds are used to obtain a signal level dependent on the quantity of label in the measured state.

In general, it is desirable in designing a specific binding assay to aim at high sensitivity, adaptability of the form of the assay so that it can be applied to a wide variety of specific binding pairs and hence substances to be assayed, and reduction of the number of manipulations involved in carrying out the assay to give simplicity in use.

It is difficult to achieve all these aims at once. For example, some highly sensitive assays involving the successive binding of analyte and labelled binding partner to a solid specific adsorbent require an inconveniently large number of successive manipulations in use. On the other hand other assays, especially fluoroimmunoassays, in which (in some cases) all the necessary reactions can take place in a single liquid reaction phase without the need for separation steps, may be less sensitive than desired because of extraneous absorptions, scatterings and light emissions by irrelevant constituents of the assay system (serum, containing vessel, etc.)

It has already been proposed to improve the sensitivity of fluoroimmunoassays by using as the fluorescent labelling substance a chelated derivative of a rare earth metal ion, such as europium, which shows light emission of long lifetime upon excitation, and which can therefore be detected by a measuring instrument which is relatively much less sensitive to short-lived interfering light emissions (E. Soini and I. Hemmilä, Clin. Chem. (1979) 25 (3) 353–361, and I. Hemmilä, E. Soini and T. Lövgren, Fresenius Z. Anal. Chem. (1982) 311, 357). Such an available instrument is for example the Perkin-Elmer LS-5 (Trade Mark) luminescence spectrometer, capable of gating out detection of short-lived luminescence, and of selectively detecting light emitted within a time segment of variable width up to 13.3 milliseconds after pulse excitation of the sample.

It is considered by the present inventors, however, that this proposal is still subject to certain limitations of its applicability, in the first place because of the limited stability of the metal chelates when used as labels at low concentration and in the second place because the light emission of such chelates when used to label antibodies is considered not significantly quenchable or enhanceable in response to the formation of immune complexes, as for example is the fluorescence of fluorescein. Hence the chelates are not generally applicable to the preparation of quenched-fluorescence assay systems such as those described for example in U.S. Pat. No. 4,160,818.

A specific binding assay according to this invention utilises, as the labelled substance, one of the relevant specific binding partners in the form of a derivative linked to a luminescent substance which shows delayed light emission upon photoexcitation, with a lifetime greater than 1 microsecond, (and usally in the range 10–13000 microseconds), the delayed light emission of which is subject to quenching by molecular oxygen, and the amount of the labelled substance present in the assay reaction mixture (or relevant portion thereof) is measured by a time-resolved photometric method in the presence of a quench-inhibiting substance able to prevent quenching by molecular oxygen.

It is a surprising and advantageous feature of the present assays that it is possible to find quench-inhibiting substances which can be present in the reaction liquid and allow the use of room-temperature, open-atmosphere conditions. The effects of particular examples of such substances, e.g. sulphites, bisulphites and metabisulphites, are described in greater detail below.

We find that this form of assay has several advantages. Thus, the labelling substance can be chosen from a variety of stable labels, as described below. A plurality of such labels also show modification of their luminescent properties upon complex formation and can thus, of desired, be made part of a single-liquid-phase, luminescence-quench time-resolved luminescence immunoassay or other binding assay, which to our knowledge has not previously been achieved. Furthermore, the use of the quench-inhibiting substance makes it unnecessary to provide for oxygen-free conditions by such complex manipulations as bubbling with inert gas, or carrying out the measurement in vacuo.

In general, we believe that most convenient assays of the form described herein will preferably call for luminescent substances which upon pulse excitation continue to yield luminescence after a time delay of at least about 50 microseconds after the end of the excitation. In general, it is preferred that the time-delayed measurement of luminescence should be placed and determined in length in relation to the luminescence lifetime of the label, so that as much as conveniently possible of the luminescence yield can be detected. Where the particular luminescence instrument mentioned above (P-E LS-5) is used, luminescence measurement can last up to 13.3 milliseconds from the end of the pulse excitation.

Suitable luminescent substances for use in this invention may be selected from those showing $O_2$-quenchable fluorescence, or phosphorescence, or both. examples include halogenated derivatives, especially brominated and/or iodinated derivatives, of fluorophors. Notable examples of these are halogenated, especially brominated and/or iodinated, derivatives of fluorescein, e.g. erythrosin and eosin. Erythrosin, giving a stronger signal, is preferred to eosin.

Also usable as delayed luminescence labels are fluorophors in the presence, in the reaction or measurement medium, of soluble compounds of heavy atoms, at about 1M concentration, e.g. sodium and potassium iodide, sodium or potassium bromide or iodide, caesium bromide or iodide, lead acetate, thallium acetate, or lead thallium acetate.

It is necessary to overcome the quenching effect of atmospheric oxygen in order to utilise delayed luminescence in the present assays, and this can be achieved by adding a quench-inhibiting substance, e.g. a reducing substance able to prevent the quenching effect of oxygen. Two suitable examples of such substances are a metabisulphite, such as sodium metabisulphite, and a sulphite, such as sodium sulphite. These substances can suitably be present in the assay system in solution at concentrations in the order of $10^{-2}M$. Ascorbic acid, thiosulphate and dithionite have however been found unsuitable in experiments carried out to date.

Other available methods of obtaining oxygen-free conditions include, for example, the use of enzyme-substrate systems as reducing substances to reduce oxygen content of the reaction mixture or otherwise overcome the oxygen quench effect, e.g. glucose+glucose oxidase+catalase, or glucose+glucose oxidase+peroxidase substrate+peroxidase.

We find that stronger signals are obtained when the reaction mixture or other material subjected to luminescence photometry contains protein at concentrations of the order of 1 g/l and further enhancement is found then a detergent, e.g. a non-ionic detergent such as Triton X-100 (which is a polyoxyethylenated (9-10 units/molecule) $C_8$-alkylphenol), is present, for example at concentrations of the order of 1 g/l.

The preparation of labelled materials for use in the present assays can generally be carried out in a manner analogous to the methods used to prepare labelled materials for previous binding assays. For example, erythrosin isothiocyanate and eosin isothiocyanate can be directly coupled to any of a large number of proteins and haptens needed in binding assays, using available procedures. Other derivatives of luminescent labelling materials, e.g. the carboxylic acids, can be coupled using many of the widely available coupling materials.

The assays of this invention are particularly convenient for the immunoassay or other specific binding assay of substances present in biological fluids such as blood serum or urine, and measurements can be carried out without the need to separate bulk serum components.

Accordingly, in certain embodiments, an assay according to the invention comprises subjecting a sample derived from a biological fluid, such as blood serum or urine, to an immunological or other specific binding reaction with a specific binding partner of the analyte of interest, and letting the extent of this binding reaction determine the extent of complex formation by a corresponding binding material labelled with a luminescent label, and then directly or indirectly measuring by photometry the amount or distribution of the luminescent-labelled material in its free and/or complexed forms, characterised in that the labelling luminescent substance is a covalently-linked organic luminescent substance which is capable of giving delayed luminescence upon excitation by light with a wavelength greater than 400 nm (usually greater than 450 nm), and which is subject to quenching by molecular oxygen, and in that the measurement of the luminescent label is carried out by time-resolved luminescence photometry in the presence of a reducing substance, or other quench-inhibiting substance, capable of preventing quenching of the luminescence by molecular oxygen.

These embodiments of the invention include for example immunoadsorbent immunoassays in which the reaction materials comprise (i) an immunoadsorbent capable of specifically binding the analyte, (ii) the luminescent-labelled analogue of the analyte and (iii) the quench-inhibiting substance capable of preventing the quenching by oxygen of the luminescence from the labelled material: the assay can then be carried out for example by allowing the binding reactions to take place with the biological fluid sample and components (i)-(iii) in contact with each other, then separating the reaction liquid from the immunoadsorbent and measuring its luminescence under the conditions mentioned herein.

The dosages of the immunoadsorbent and the luminescent-labelled analogue in such an assay are set, matched to each other and calibrated by methods well known in themselves. They are often adjusted so that about half the label (e.g. about 20-80%) remains in solution in the absence of analyte, and so that the presence of a very small incremental quantity of analyte, at the limit of sensitivity of the assay, causes a marginal quantity of label to remain in solution at the end of the binding reaction.

An alternative example, a homogeneous assay, uses the following materials: (i) a specific binding partner of the analyte in soluble form, yielding a soluble binding complex with the analyte, (ii) the luminescent-labelled analogue of the analyte and (iii) the substance capable of preventing the quenching by oxygen of the luminescence from the labelled material. The labelled analogue (ii) and specific binding partner (i) are selected so that their complex with each other exhibits as little luminescence as possible, e.g. when component (i) is an antibody it is selected for its ability to quench the luminescence of component (ii) as completely as possible by immune complex formation, (a quenching which is exhibited also in the complete absence of oxygen). Then in this assay the measurement of luminescence can immediately follow on from the completion of the binding reaction without the step of removal of a solid phase, and the components (i) and (ii) are dosed and matched so that in the absence of analyte the luminescence of the label is about half-maximally quenched or enhanced, (e.g. about 20-80%) by binding with component (i), while the presence of a very small incremental quantity of the analyte, in the assay, causes a diminution in the degree of this quenching.

It is apparent from the description given above that this invention is not particularly limited by the individual identity of the analyte and the specific binding reactions in which it takes part. The range of analytes for which assays can be made according to the invention includes for example:

drugs, e.g. anticonvulsant/antiepileptic substances, such as primidone, phenytoin, phenobarbitone, carbamazepine, ethosuximide, valproic acid;

antibiotics, e.g. aminoglycosides such as gentamicin, tobramycin, amikacin, netilmicin and sisomycin;

antiasthamatic substances, e.g. theophylline; cardioactive or antiarrhythmic substances and related substances, e.g. quinidine, propranolol, oxprenolol, procainamide and its N-acetyl metabolite, lignocaine, digoxin, digitoxin;

Hormonally-active substances and related materials, e.g. thyroid hormones, steroid hormones, e.g. oestriol and its conjugates such as oestriol sulphate, progesterone, oestradiol, oestrone-3-glucuronide, other steroids, bile acids, and cholesterol;

proteins and peptide hormones such as insulin, glucagon, human placental lactogen, human growth hormone, human serum albumin, immunoglobulins such as IgG, IgE, IgA, IgM, $\beta_2$-microglobulin, thyroid-binding globulin, corticosteroid-binding globulin; hepatitis antigens and antibodies, such as HB surface antigen and corresponding antibody.

In the case of those substances listed above which are not themselves immunogenic, antibodies can be raised in known manner against their conjugates with a protein such as serum albumin. As with previous forms of immunoassay it is desirable then to form congugates of the analytes, where needed, with the luminescent label by derivatisation at the same site in the analyte molecule as previously derivatised for conjugation with protein in order to raise antibody.

The invention is illustrated by the following non-limitative Examples.

EXAMPLE 1

Non-separation (homogeneous) assay of primidone (a) Instrumentation

A Perkin-Elmer Model LS-5 luminescence spectrometer was used. Experiments were performed in polystyrene test tubes (No. 484, 55×12 mm) from Sarstedt, Leicester, U.K.. Sample solution volumes were 1.5 ml unless otherwise stated. An adapter, as described by Kamel, R. S., Landon, J., and Smith, D. S. (Clin. Chem. (1980) 26, 1281–1284), was placed in the cuvette compartment of the spectrometer to enable measurements to be made directly on solutions in the test tubes.

The prompt and delayed fluorescence of erythrosin were measured with excitation and emission wavelengths of 536 and 560 nm, respectively, with monochromator slit-width settings of 5 and 10 nm, respectively. Phosphorescence was measured with excitation and emission wavelengths of 536 and 690 nm, respectively, with monochromator slit-width settings of 5 and 20 nm, respectively. In measurements of delayed fluorescence and phosphorescence, a delay time ($t_d$) of 40 us and a gate time ($t_g$) of 300 us were selected. (The delay time is the time between the excitation light pulse and the start of measurement. The gate time is the time interval over which the signal is subsequently measured after each light pulse.) The instrument was used with "response" setting number 2, and measurements were made using the "integration mode" facility, total measurement time being 4.2 s in all cases. All results were expressed on an arbitrary scale of luminescence intensity: it was found convenient to arrange the concentrations of reactants so that in the assays the maxiumum luminescence signal observed was of the order of 2.5, and the assay conditions particularly mentioned below correspond to this recommendation.

(b) Control Measurements in aqueous buffer

Sodium phosphate buffer (100 mmol/l, ph 8.0) was used throughout. Erythrosin (Sigma, Poole, Dorset, U.K.) was dissolved in buffer to 5 $\mu$mol/l concentration. The following phosphorescence signals were measured:

| Sample | Signal |
---|---
| Erythrosin in buffer | 0.011 |
| Erythrosin in buffer after exhaustive bubbling with oxygen-free nitrogen | 0.35 |
| Erythrosin in buffer after addition of a small amount of solid carbon dioxide ("dry ice") | 7.30 |

The signal increase following nitrogen bubbling results from purging of oxygen from the solution. The signal increase after dry ice addition probably reflects both oxygen purging and temperature reduction of the solution.

(c) Control Measurements in aqueous buffer with additives

Sodium phosphate buffer (100 mmol/l, ph 8.0) was used throughout.

(i) Proteins

The phosphorescence of erythrosin (5 $\mu$mol/l) in buffer was measured in the presence of bovine serum albumin (BSA) or bovine thyroglobulin (BTG) (both proteins from Sigma, Poole, Dorset, U.K.).

| Additive | Signal |
---|---
| BSA (1 g/l) | 2.25 |
| BSA (2 g/l) | 2.35 |
| BSA (10 g/l) | 4.23 |
| BTG (1 g/l) | 2.72 |
| BTG (2 g/l) | 3.24 |
| BTG (5 g/l) | 5.73 |

(ii) Sodium sulphite and sodium metabisulphite

The phosphorescence of erythrosin (1 $\mu$mol/l) in buffer containing 1 ml/l Triton x-100 detergent (BDH, Poole, Dorset, U.K.) was measured in the presence of sodium sulphite or sodium metabisulphite (both from BDH, Poole, Dorset U.K.).

| | Signal |
---|---
| Additive | |
| Sodium sulphite (1 g/l) | 36.4 |
| Sodium metabisulphite (1 g/l) | 35.4 |
| Additive(s) | |
| Sodium sulphite (1 g/l) | 0.79 |
| Sodium sulphite (1 g/l), BSA (1 g/l) | 2.65 |
| Sodium sulphite (1 g/l), Triton x-100 (1 ml/l) | 3.50 |

The phosphorescence of erythrosin (100 nmol/l) in buffer was measured in the presence of sodium sulphite, with or without other additives.

(iii) Glycerol

The phosphorescence of erythrosin (100 nmol/l) was measured in a mixture of glycerol (15 parts by volume) and buffer containing BSA (1 g/l) (one part by volume). A signal of 2.55 units was recorded.

(d) Preparation and calibration of materials

1. Preparation of erythrosin-labelled primidone

The 4-aminophenyl derivative of primidon was prepared by nitration and reduction of primidone following the procedures of Bousquet, E. W. and Adams, R. (J. Amer. Chem. Soc. (1930) 52, 224–229).

The primidone derivative (3 mg) was dissolved in 300 $\mu$l of dimethylformamide containing 10 ml/l triethylamine. Erythrosin-5-isothiocyanate from Molecular Probes, Junction City, OR, U.S.A. (18 mg) was dissolved in 300$\mu$l of the same solvent. The two solutions were mixed and reaction allowed to proceeed overnight in the dark at room temperature. The reaction mixture was then applied to a preparative silica-gel thin-layer chromatography plate (Whatman, type PLK5F) which was developed with chloroform/methanol/glacial acetic acid (70:25:5 parts by volume). The area of the major product band was scraped from the plate and the product eluted into methanol.

The concentration of the erythrosin-labelled primidone product was estimated by optical density measurement after dilution in sodium phosphate buffer (100 mmol/l, pH 8.0), assuming an extinction coefficient of $8.3 \times 10^4$ l mol$^{-1}$ cm$^{-1}$ at 540 nm (Moore, C., Boxer, D., and Garland, P., F.E.B.S. Letters (1979) 108, 161–166).

The methanolic product solution was stored at $-20°$ C.

2. Preparation of anti-primidone serum

The amino-derivative of primidone at the phenyl 4-position was diazotised and coupled to BSA following established procedures. Sheep were injected with the resulting immunogenic conjugate to raise anti-primidone serum.

3. Diluent buffer

Sodium phosphate buffer (100 nmol/l, pH 8.0) containing sodium sulphite (2 g/l), BSA (1 g/l), and sodium azide (1 g/l) was used throughout unless otherwise stated.

4. Antibody dilution curves

An immunoglobulin fraction of a sheep anti-primidone serum was prepared by the conventional sodium sulphate precipitation method. The immunoglobulins (containing the specific antibodies to primidone) were resuspended to the original serum volume in diluent buffer. Doubling dilutions of the immunoglobulins were prepared.

To 100 µl of each immunoglobulin dilution was added 100 µl of erythrosin-labeled primidone (to give final concentration 120 nmol/l). after incubation for 30 min at room temperature, 1.4 ml of diluent buffer was added. After a further 5 min at room temperature, phosphorescence and delayed fluoresence were measured as described above (Example 1). The experiment was also carried out using the immunoglobulin fraction from a normal sheep serum as a non-specific control.

The results (FIG. 1) show that binding of the labelled primidone by specific antibodies to primidone leads to quenching of both the phosphorescence and the delayed fluorescence by a maximal extent of about 80%. There was no effect of non-specific sheep immunoglobulins.

(e) Assay Standard Curves

Assay standards were prepared by dissolving primidone in pooled normal human serum (ILS, Newbury Street, London EC1,U.K.).

To 10 µl of each serum standard was added 100 µl of erythrosin-labelled primidone (to give final concentration 120 nmol/l), followed by 100 µl of anti-primidone immunoglobulins (diluted 18.6-fold). After incubation for 30 min at room temperature, 1.4 ml of diluent buffer was added (final dilution of the immunoglobulins: 300-fold). After a further 5 min at room temperature, phosphorescence and delayed fluorescence were measured.

The resulting standard curves (FIG. 2) show that primidone in the serum standards competes with the labelled primidone for binding to the limited amount of antibodies to primidone. The more unlabelled drug present, the greater the proportion of the labelled primidone that remains free (non-antibody-bound) after completion of the binding reactions, and hence the greater the phosphorescence or delayed fluorescence signal.

The effect of serum on the standard curves was checked in the following way. To 10 µl of each primidone serum standard was added either 100 µl of diluent buffer or 100 µl of pooled normal human serum, followed by 100 µl of erythrosin-labelled primidone, then 100 µl of anti-primidone immunoglobulins (diluted 18.6-fold). After incubation for 30 min at room temperature, 1.4 ml of sodium phosphate buffer (100 nmol/l, pH 8.0) containing sodium sulphite (10 g/l), BSA (1 g/l), and sodium azide (1 g/l) was added. After a further 5 min at room temperature, phosphorescence was measured.

The results (FIG. 3) show that the additional presence of up to 100 µl of human serum in the assay mixtures has a negligible effect on the standard curve.

EXAMPLE 2

Solid-phase separation assay of primidone (with measurement of the free fraction of the labelled primidone)

The instrumentation and control measurements given in connexion with Example 1 are applicable also this Example.

(a) Erythrosin-labelled primidone, anti-primidone serum, and primidone serum standards These reagents were prepared as described above (Example 1).

(b) Anti-primidone magnetisable solid-phase

Sheep anti-primidone serum was coupled to magnetisable cellulose/iron oxide particles at a coupling ratio of 2 ml of antiserum per g solid phase using the cyanogen bromide technique. The solid-phase particles were prepared, and coupling carried out, as described by Pourfarzaneh, M., Kamel, R. S., Landon, J., and Dawes, C. C. (Meth. Biochem. Anal. (1982) 28, 267–295).

(c) Diluent buffer

Sodium phosphate buffer (100 nmol/l, pH 8.0) containing sodium sulphite (2 g/l), BSA (1 g/l), and sodium azide (1 g/l) was used throughout unless otherwise stated.

(d) Antibody dilution curve

Doubling dilutions of anti-primidone solid-phase suspensaion were prepared.

To 100 µl of each solid-phase dilution was added 100 µl of erythrosin-labelled primidone (120 nmol/l). After incubation for 30 min at room temperature with constant mechanical shaking (to keep the solid-phase particles in suspension), 1.4 µl of diluent buffer was added and the particles sedimented on a permanent block magnet. The phosphorescence of the supernatants above the sedimented particles was measured.

The results (FIG. 4) show the extent of binding of the labelled primidone by various amounts of the anti-primidone solid phase.

(e) Assay Standard Curves

To 10 microliter of primidone serum standard or 10 microliter of primidone standard prepared in diluent buffer was added 100 microliter of erythrosin-labelled primidone (to give final concentration 120 nmol/l), followed by 100 microliter of anti-primidone solid-phase suspension (25 g/l). After incubation for 30 min at room temperature with constant mechanical shaking, 1.4 ml of diluent buffer was added and the particles sedimented magnetically as above. The phosphorescence of the supernatants above the sedimented particles was measured.

There was no significant difference between the resulting standard curves obtained with standards prepared in serum or in diluent buffer. This indicates that serum components present in the assay supernatants have no effect on the measurement of the phosphorescence of the free labelled primidone.

In buffer containing albumin (5g/l), sodium sulphite (12g/l) and sodium azide (3g/l), the phosphorescence detection limit in our examples was found to be 560 picomolar for erythrosin and 165 picomolar concentration for erythrosin-primidone conjugate. Phosphorescence lifetimes were estimated as 210 microseconds and 250 microseconds respectively.

We found that the presence of azide stabilised the erythrosin phosphorescence in the presence of sulphite against the effects of the temporary presence of air due to dissolution on shaking : e.g. when the solution was shaken in air in absence of azide the phosphorescence was temporarily quenched but returned over 2-3 minutes. Azide prevented this temporary quenching.

EXAMPLES 3, 4 and 5

Adaptation of the assays described above, to the cases of carbamazepine (Ex.3), thyroxine ("T4") (Ex.4) and cortisol (Ex.5), can be carried out for example by using appropriate standard preparations of the respective anti-drug or anti-hormone serum or immunoglobulin in place of the anti-primidone sera used above, and conjugates of erythrosin with the respective analyte. The needed conjugates can be made by known procedural steps and/or as indicated below.

(a) Preparation of erythrosin-labelled carbamazepine derivatives

Iminostilbene (1.93 g) is dissolved in anhydrous toluene (50 ml). This solution is added dropwise with stirring to 10 ml of a 12.5% w/w solution of phosgene in toluene (1.1 g of phosgene) and the mixture heated under reflux with exclusion of moisture for 1 h. To the solution at 0° C. is added 1.3 ml (1.2 g) of freshly re-distilled ethylenediamine and the mixture heated under reflux with exclusion of moisture for 3h. On cooling to 0° C. a white precipitate forms, and is separated by filtration. The filtrate is evaporated to dryness under vacuum then extracted into dilute hydrochloric acid from chloroform. The inorganic extract is basified with concentrated ammonia and re-extracted with chloroform. The organic extract is dried ($Na_2SO_4$) and evaporated to dryness to yield carbamazepine-N-beta-ethylamine, 1.6 g.

Other carbamazepine-N-alkylamines can be -prepared by the same method, substituting 1,3-propanediamine, 1,2-propanediamine lpropylenediamine) or 1,6-hexanediamine (hexamethylenediamine) for the ethylenediamine.

Each carbamazepine-N-alkylamine derivative can then be reacted with erythrosin-5-isothiocyanate and the reaction mixtures separated by silica-gel thin-layer chromatography following known standard procedures. Erythrosin-labelled carbamazepine products can suitably be eluted from the silica gel into methanol and stored at −20° C. until required for use, and then diluted into suitable buffer, e.g. sodium phosphate 0.1M, pH8, with 0.2% Triton X-100 and 0.3% sodium azide.

(b) Preparation of T4-Erythrosin

L-thyroxine from Sigma (4.35 mg) is dissolved in 100 microliter methanol containing 10 ml/l triethylamine, and 10 microliter 1M NaOH. Erythrosin isothiocyanate from Molecular Probes, USA (2.5 mg) is dissolved in 100 microlitre methanol containing 10 ml/l triethylamine. The two solutions are mixed and the reaction allowed to proceed for 3 hours in the dark. The reaction mixture is then applied to a preparative silica-gel TLC plate (Whatman, type 5637) which is developed with chloroform/methanol/ammonia (8:6:3). The major band is scraped off and the product eluted into methanol.

The concentration of T4-erythrosin can be estimated by optical density measurement after dilution in sodium phosphate buffer (100 millimolar, pH 8.0 containing 0.2% Triton X-100 and 0.3% sodium azide) assuming an extinction coefficient of $8.3 \times 10^4$ l $mol^{-1}$ $cm^{-1}$ at 540 nm.

(c) Preparation of erythrosin-labelled cortisol

Commercially available cortisol 21-hemisuccinate can be coupled to erythrosin-thiocarbamyl-ethylene diamine (prepared in analogous manner to the well-known preparation of fluorescein thiocarbamyl-ethylene-diamine), by means of a carbodiimide coupling reaction in dimethylformamide solution in analogous manner to well-known standard procedures.

It is found that these assays for carbamazepine, thyroxine and cortisol give comparable sensitivity levels as the assay for primidone from which they are derived by adaptation. Effective sensitivity can be increased in use if need be, especially in the case of cortisol, by the use of greater volumes of patient-derived serum than described above for primidone.

Corresponding assays can be derived by adaptation for a wide range of other substances, especially for example gentamicin, tobramycin, amikacin and netilmicin.

In particular, useful adaptations of the assays described above can be made by the use (instead of erythrosin) of 4-methyl umbelliferone, or other fluorescent coumarins or flavones, and halogenated, especially for example brominated or iodinated, derivatives thereof, using appropriate chemical coupling steps known in themselves for forming conjugates and not in themselves constituting a part of this invention. For 4-methylumbelliferone conjugates it is convenient to measure the delayed fluorescence at 450 nm upon excitation at 380 nm, using a gated detector sensitive as from after about 40 microseconds after an excitation pulse and continuing to be sensitive for about 300 microseconds thereafter.

EXPLANATION OF THE GRAPHS FORMING FIGS. 1-5 OF THE ACCOMPANYING DRAWINGS

FIG. 1 shows antibody dilution curves, showing quenching of phosphorescence (one form of delayed luminescence) and delayed fluorescence (another form of delayed luminescence) of erythrosin-labelled primidone by antibodies to primidone. The horizontal axis gives values of final dilution of the antibodies. The vertical axis gives observed luminescence values as a percent of the value obtained without immunoglobulins present. Curve A shows phosphorescence obtained in the presence of nonspecific sheep immunoglobulins (control). Curve B shows delayed fluorescence, and curve C shows phosphorescence, in each case as obtained in presence of antibodies to primidone in the indicated dilution.

Figure 2:
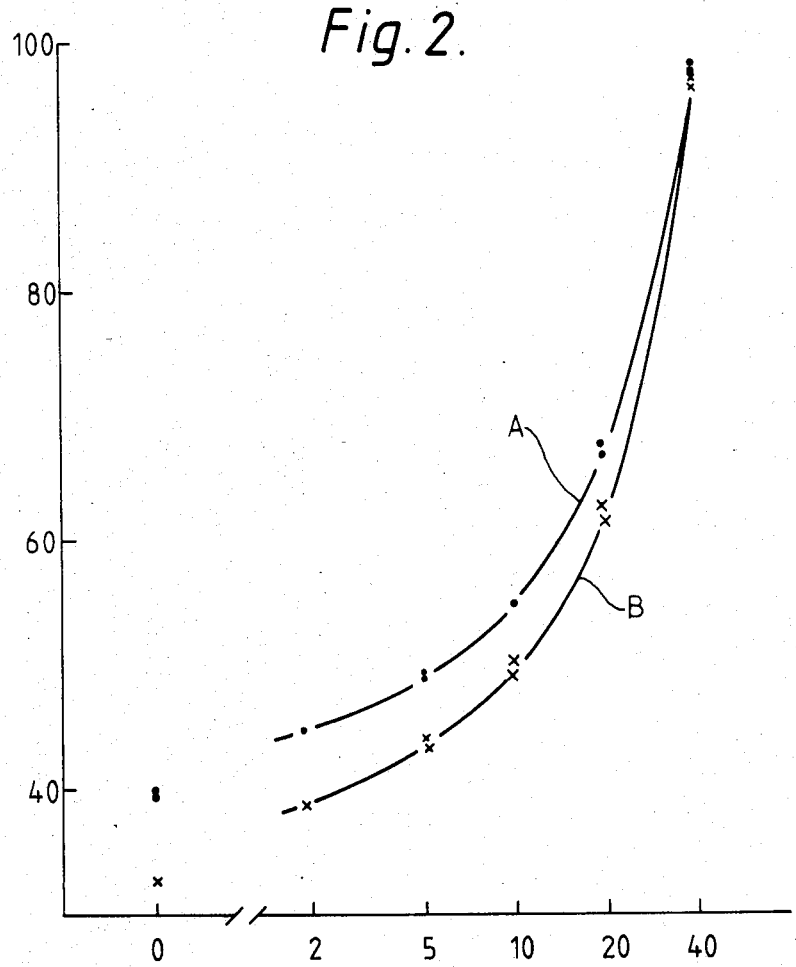

FIG. 2 shows standard curves for non-separation (homogeneous) assay of primidone in serum, with measurement of phosphorescence or delayed fluorescence of erythrosin-labelled primidone. The horizontal axis gives primidone concentration (standard) (milligram/liter). The vertical axis has the same significance as in FIG. 1. Curves A and B represent results from phosphorescence detection and delayed fluorescence detection respectively.

Figure 3:
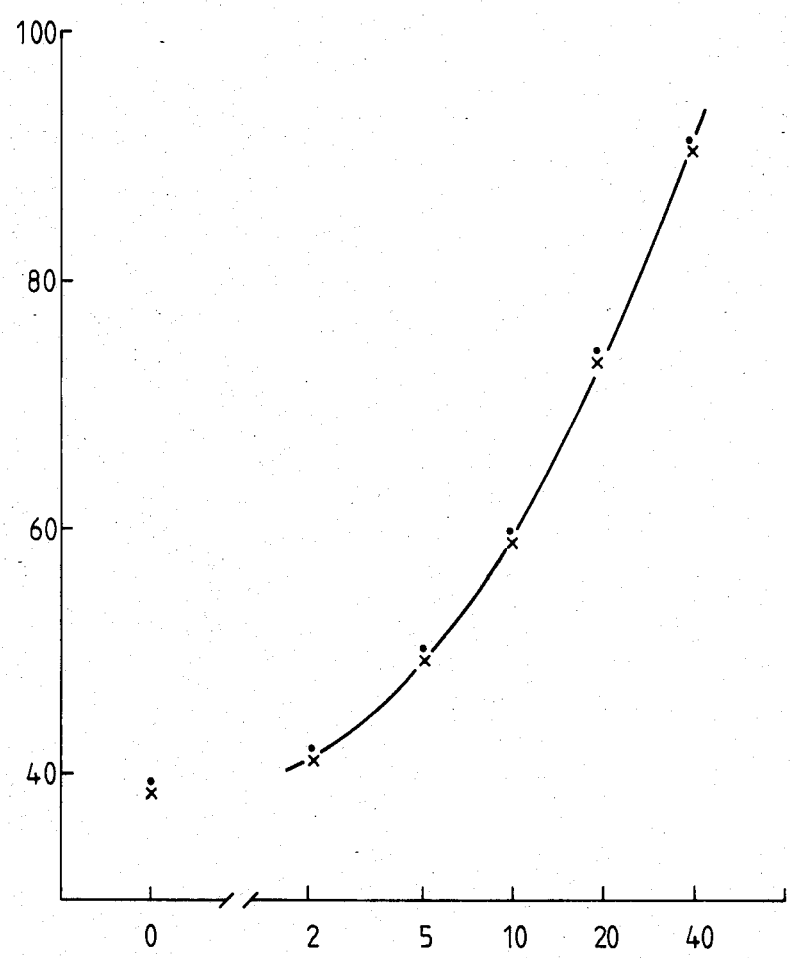

FIG. 3 shows standard curves for nonseparation (homogeneous) assay of primidone, showing lack of serum effect. The axes have the same meaning as in FIG. 2. The dotted points show the results obtained in presence of 100 microliter serum in each reaction mix : the crossed points the control values with 100 microliter buffer.

Figure 4:
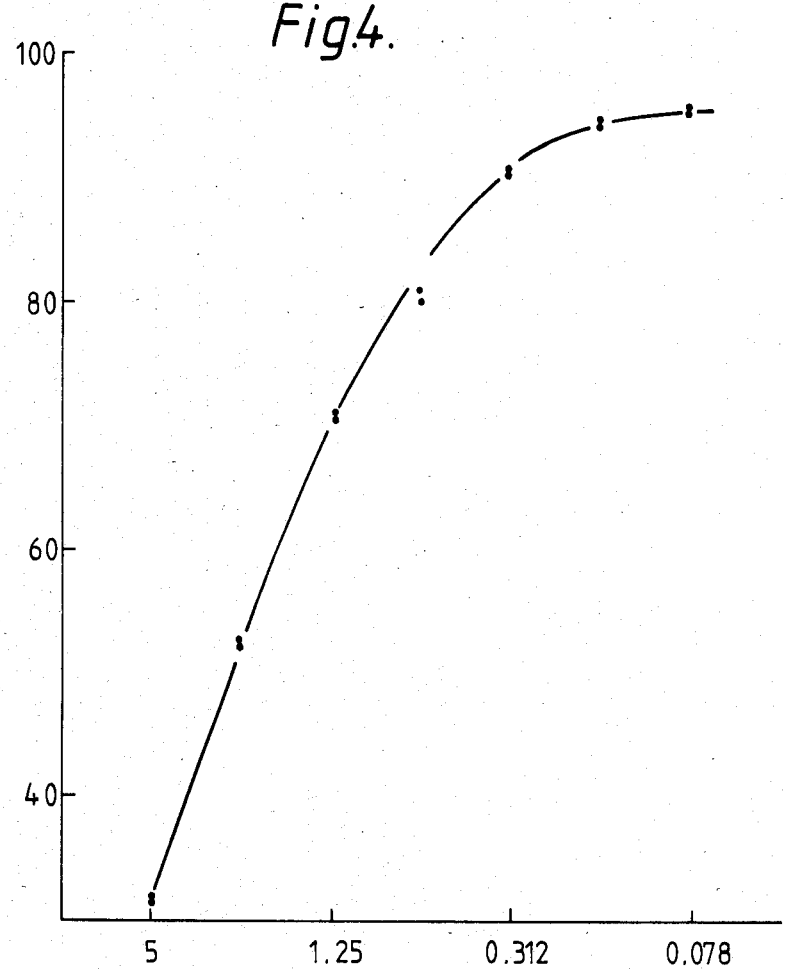

FIG. 4 gives an antibody dilution curve showing the binding of erythrosin-labelled primidone by anti-primidone solid phase. The horizontal axis indicates the amount of solid-phase particles per tube (mg). The vertical axis indicates the luminescence signal as a per cent of signal as obtained in the absence of solid phase.

Figure 5:
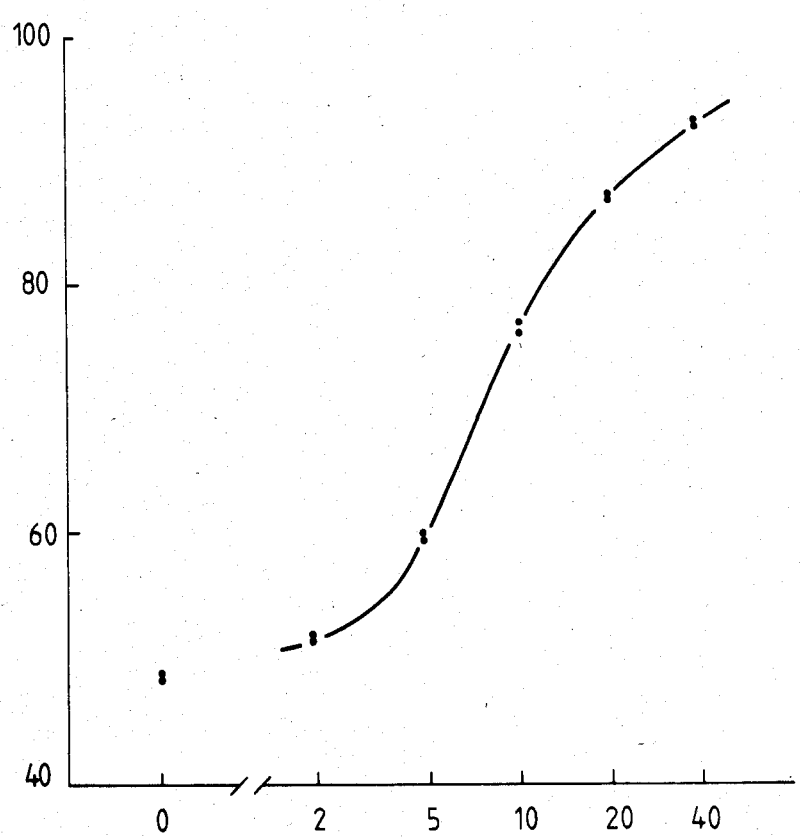

FIG. 5 gives a standard curve for the solid-phase (separation) assay of primidone in serum with measurement of the phosphorescence of the free fraction of the labelled primidone. The horizontal axis means the same is in FIGS. 2-3. The vertical axis means the same as in FIG. 4.

We claim:

1. In a process of carrying out a specific binding assay, for the qualitative detection or quantitative or semi-quantitative determination of an analyte which forms a component of a specific binding reaction, using a labelled conjugate form of a derivative or analogue of one of the relevant specific binding partners, said labelled form being capable of emitting delayed luminescence upon photo-excitation, the improvement which comprises using, as the labelled conjugate form of one of the relevant specific binding partners, a derivative or analogue of the specific binding partner with a derivative of a luminescent substance which shows a delayed light emission upon photoexcitation, the delayed light emission of which is subject to quenching by molecular oxygen, and carrying out the assay using a time-resolved photometric method in the presence of an effective amount of a quench-inhibiting substance able to prevent quenching by molecular oxygen, said quench inhibiting substance comprising sodium sulphite, bisulphite or metabisulphite present in the assay reaction mixture at a concentration of the order of $10^{-2}M$ and the luminescent substance being selected from derivatives of brominated and iodinated fluorophors, and fluorescent coumarins and flavones, and their brominated and iodinated derivatives.

2. A process according to claim 1, wherein said derivative of a luminescent substance comprises erythrosin (isothiocyanate).

3. A process according to claim 1, wherein the assay utilises an immunoadsorbent and separation of free from bound conjugate.

4. A process according to claim 1, wherein the assay utilises a specific binding partner of the labelled conjugate which quenches the luminescence of the conjugate upon binding therewith.

5. A process according to claim 1, wherein the analyte is selected from the group consisting of primidone, phenytoin, phenobarbitone, carbamazepine, ethosuximide and valproic acid; gentamicin, tobramycin, amikacin, netilmicin and sisomycin; theophylline; quinidine, propranolol, oxprenolol, procainamide, N-acetyl procainamide, lignocaine, digoxin and digitoxin; oestriol sulphate, progesterone, oestradiol, oestrone-3-glucuronide; bile acids and cholesterol; and proteins and peptide hormones.

6. A test kit or reagent set for carrying out a specific binding assay which comprises a kit assembly including (i) a labelled conjugate form of one of the relevant specific binding partners comprising a derivative or analogue of the specific binding partner with a derivative of a luminescent substance which shows a delayed light emission upon photoexcitation, the delayed light emission of which is subject to quenching by molecular oxygen, and (ii) an effective amount of a quench-inhibiting substance able to prevent the oxygen quenching of the luminescence of component (i) said quench inhibiting substance comprising sodium sulfite, bisulfite or metabisulfite and the luminescent substance being selected from derivatives of brominated and iodinated fluorophors, and fluorescent coumarins and flavones, and their brominated and iodinated derivatives.

* * * * *